United States Patent [19]

Watanabe et al.

[11] 4,436,428

[45] Mar. 13, 1984

[54] PHOTOACOUSTIC SPECTROMETER

[75] Inventors: Atsuo Watanabe; Masahiro Uno, both of Kawasaki, Japan

[73] Assignee: Fuji Electric Co., Ltd., Kawasaki, Japan

[21] Appl. No.: 210,407

[22] Filed: Nov. 25, 1980

Related U.S. Application Data

[63] Continuation-in-part of Ser. No. 55,271, Jul. 6, 1979, abandoned, and a continuation-in-part of Ser. No. 55,272, Jul. 6, 1979, abandoned, and a continuation-in-part of Ser. No. 58,207, Jul. 17, 1979, abandoned.

[51] Int. Cl.³ .................................... G01N 21/00
[52] U.S. Cl. .................................... 356/432; 356/440; 250/343; 250/345; 250/351
[58] Field of Search ............... 356/432, 437, 440; 250/343, 344, 345, 346, 350, 351, 352

[56] References Cited

U.S. PATENT DOCUMENTS

| | | | |
|---|---|---|---|
| 3,560,738 | 2/1971 | Strange | 250/343 |
| 3,758,786 | 9/1973 | Weinel | 250/343 |
| 3,811,782 | 5/1974 | Kerr | 356/432 |
| 3,948,345 | 4/1976 | Rosencwaig | 356/432 |
| 4,019,056 | 4/1977 | Block et al. | 250/344 |
| 4,028,932 | 6/1977 | Rosencwaig | 73/67.2 |
| 4,067,653 | 1/1978 | Fletcher et al. | 250/344 |
| 4,253,770 | 3/1981 | Horiba | 356/437 |

FOREIGN PATENT DOCUMENTS

| | | | |
|---|---|---|---|
| 816849 | 7/1959 | United Kingdom | 250/343 |

OTHER PUBLICATIONS

Schleusener et al. "Differential Spectrophone Measurement of the Absorption of Laser Energy by Atmospheric Dust" *Applied Optics* vol. 14, No. 11 (Nov. 1975) pp. 2564–2565.

*Primary Examiner*—R. A. Rosenberger
*Attorney, Agent, or Firm*—Bruce L. Birchard

[57] ABSTRACT

By the use of one or more beams of chopped, variable-frequency, monochromatic light to illuminate the sample chamber of at least one gas-filled cell including such sample chamber and a reference chamber joined to the sample chamber by a tunnel-like opening or orifice which permits fluid communication between the chambers and incorporating a thermal-flowmeter-type sensor element in the path of flow of the fluid between the chambers of each such cell, the compositional characteristics of one or more samples in each sample chamber can be determined accurately.

1 Claim, 44 Drawing Figures

PHOTOACOUSTIC SPECTROMETER

RELEVANT CO-PENDING APPLICATIONS

This application is a continuation in part of three co-pending applications Ser. No. 55,271 filed July 6, 1979, Ser. No. 55,272 filed July 6, 1979 and Ser. No. 58,207 filed July 17, 1979, all having the same co-inventors as this application and all now abandoned.

BACKGROUND OF THE INVENTION

1. Field of the Invention

This invention relates to spectrometers and, more particularly, to photoacoustic spectrometers.

2. Prior Art

The broad concept of analyzing substances through the use of photospectroscopy is quite old. For example, see the article *Photoacoustic Spectroscopy of Solids* written by allan Rosencwaig and appearing in the magazine PHYSICS TODAY for September 1975. That article gives a good historical perspective of the technique and its advantages over destrictive spectrographic techniques. It also distinguishes infra-red gas analyzers from photoacoustic U.S. Pat. No. 3,948,345 issued Apr. 6, 1976, to Allan Rosencwaig describes a commonly used technique. That technique involves irradiating a sample with radiant energy of variable frequency and detecting the resulting acoustical energy with a microphone. The problem with such a technique is that the microphone is sensitive to extraneous noises and other ambient conditions.

The problems of ultraviolet-visible absorption and reflectance spectrometry are well known.

Therefore, it is the general object of the present invention to overcome the problems and disadvantages experienced with prior art devices and methods.

It is a further object of this invention, to provide a material analyzing system and method which accurately gives information as to the nature of the material being analyzed.

It is a still further object of this invention to provide a method and apparatus for non-destructive analysis of non-gaseous materials of all kinds, including emulsions, solids and living organisms.

SUMMARY OF THE INVENTION

Stated succinctly, the present invention involves apparatus and techniques which permit irradiating, with visible light in a sample chamber, one or more samples of the material being studied. Single or double beans of monochromatic, variable frequency light which are chopped may be used for irradiation. An adjoining reference chamber which is not irradiated, is coupled through a tunnel or orifice to the sample chamber for fluid communication therebetween. The fluid may be a gas, for example, helium, nitrogen or air. The two chambers are hermetically sealed with respect to ambient air to form a cell. A thermal flowmeter sensor is positioned in the path of fluid flow between the sample and reference chambers. When the sample is irradiated with monochromatic, chopped light it alternately heats and cools and the heat flow causes the fluid surrounding the sample to expand and contract, resulting in a bidirectional, periodic fluid flow between the sample and reference chambers. This fluid flow is detected by the flowmeter and appears as an electrical resistance variation at the electrical terminals of the flowmeter sensor. The variation of resistance can be directly translated into an electrical signal which can be amplified and plotted with respect to irradiationenergy frequency or wavelength. The invention can be extended to multiple-cell construction for direct multiple-sample-characteristics comparison.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood by reference to the following description taken in conjunction with the accompanying drawings, in which:

FIGS. 4, 4(a), 4(b) and 4(c) are schematic diagrams of the flow detector utilized in the present invention and the electrical resistance exhibited by the respective flow elements under various conditions of fluid flow;

DETAILED DESCRIPTION OF THE PREFERRED EMBODIMENTS

Figure 1:
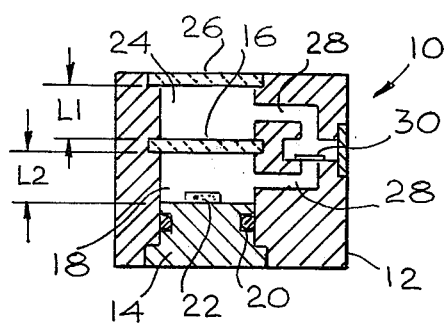
FIG. 1 is a sectional view of a photoacoustic cell according to the present invention.

In FIG. 1 photoacoustic spectrometer cell 10 includes opaque walls 12 and 14 and transparent cover 16 all hermetically sealed with respect to each other. Additionally, sample bed 18 is removably held within walls 12 by means of sealing ring 20. This combination of elements forms a sample-chamber 22 and a reference chamber 24. The two chambers communicate with one another through tunnel or orifice 26. Chambers 22 and 24 are filled with fluid, preferably a gas such as air, nitrogen or helium. A thermal flowmeter detecting element 28 is disposed along the tunnel 26, preferably at one of its ends, as shown.

Sample bed 18 carries thereon a sample 30 of the material to be analyzed. The material may be in solid, powdery, liquid or other form. Some materials, such as liquids, may require a receptacle, not shown, to confine them.

Figure 2:
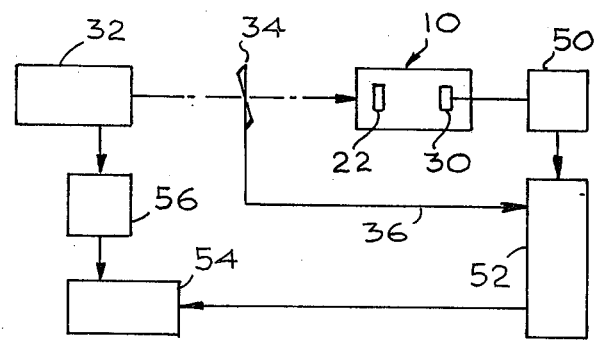
FIG. 2 is a block diagram of one embodiment of a photoacoustic spectrometer according to the present invention.

In FIG. 2 cell 10 of FIG. 1 has been placed in an operating system for photoacoustic spectrometry.

Monochromatic light source 32 provides light at a predetermined wavelength. This light may be obtained by spectral diffraction of light from a xenon lamp or from a laser of known characteristics. The wavelength should be variable over a predetermined range.

Light from source 32 is periodically interrupted by chopper 34 before it is incident upon sample 30. The chopping rate of chopper 34 is variable over a range of frequencies, for example from zero to 1000 Hz.

The light energy incident upon sample 30 through aperture 16 is absorbed, in part, by sample 30 and the absorbed light is converted into heat energy which flows into the surrounding gas in sample chamber 22, causing increased pressure in that chamber and a consequent flow of gas through tunnel 26 and past flowmeter detector element 28 into reference chamber 24 which is not illuminated and, therefore, exhibits lower pressure than sample chamber 22 during illumination of sample 30.

The interruption of illumination of sample 30 by chopper 34 causes a periodic rise and fall of the temperature of the gas in sample chamber 22 and a consequent oscillatory flow of gas through tunnel 26. The period of that oscillation is identical with the period or frequency of the chopping action by chopper 34. The frequency of the chopping action may be set anywhere between just over 0 Hz to 1000 Hz. The oscillatory flow of gas through tunnel 26 is detected by flowmeter element 28, the characteristics of which are described more fully in connection with FIGS. 3 and 4.

Figure 3:
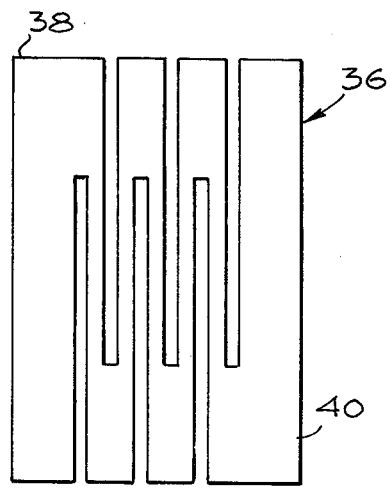
FIG. 3 is an elevational view of a flowmeter element utilized in the present invention.

In FIG. 3, grid 36 comprises a plurality of fine nickel filaments connected in electrical series between end portions 38 and 40. This grid, when subjected to an electrical current flow, serves as a hot-wire anemometer.

Two sheets 42 and 44 of the type shown in FIG. 3 are assembled into a flowmeter detector unit 28 by laminating the grids 42, 44 with glass separators 48. With electrical current flowing through the grids 42, 44 and with detector 28 in position adjacent tunnel 26 in FIG. 1, and with no illumination of sample 30, grids 42 and 44 exhibit the temperature distribution shown in FIG. 4(a). With sample 30 illuminated the temperature in chamber 22 rises, causing the gas pressure therein to rise and resulting in the flow of gas into reference chamber 24 in FIG. 1 or from left to right in FIG. 4 giving the temperature distribution shown in FIG. 4(b). When chopper 24 momentarily blocks illumination of sample 30, the pressure in chamber 22 drops and gas flows from chamber 24 back to chamber 22, in FIG. 1, or from right to left in FIG. 4, giving the temperature distribution shown in FIG. 4(c). If grids 42 and 44 are in a gas mixture comprising, for example, 5% $SO_2$, 10% He and the remainder Argon (85%), and with a current flow of 49 ma, then the temperature of nickel grid 42 rises to 100° C. and the temperature of grid 44 becomes 92° C. These grids have identical resistance-temperature characteristics. Using these two grids in combination with two fixed resistors in a Wheatstone bridge configuration the output voltage will depend upon the grid-resistance variations. Thus the oscillation of gas between chambers 22 and 24 can be detected and transformed into an electrical signal utilizing sensing element 28. This electrical signal can be pre-amplified by bridge-preamplifier circuit 50 (FIG. 2), further amplified and detected by circuit 53, which produces a d.c. voltage output without ripple by well-known techniques. That d.c. voltage is fed to computing and indicating section 52 which receives light-frequency information from control unit 56 of monochromatic light source 32 and correlates flowmeter signal output with light frequency or wavelength to produce and display a response characteristic of the type shown in FIG. 8. Frequency-voltage converters are well known and need not be described here. The voltage from the frequency-voltage converter associated with unit 56 can be used to effect the abscissa positioning of the recording element on a chart recorder, for example. in computing-indicating unit 54. The d.c. from amplifier-rectifier 52 can be used to give the recording element in that chart recorder its ordinate position.

An important difference between the present invention and photoacoustic spectrometers of the prior art is the method and apparatus by means of which the oscillatory flow of fluid (gas) between reference and sample chambers 24 and 22 is detected. Instead of using a microphone (which is sensitive to ambient noise) a plurality of hot-wire anemometers is used to form a flowmeter element, 28.

In FIG. 3, one portion of that flowmeter element is shown. Grid 36 is made of a nickel film and comprises a plurality of nickel filaments connected in series between two end portions 38 and 40.

These filaments of nickel become heated when subjected to the flow of electrical current therethrough and serve to act as a hot wire anemometer.

Two such grids 42 and 44 (FIG. 4) are supported in closely-spaced relationship with respect to each other by glass spacers 48.

With electrical current flowing through grids 42 and 44 and with static gas conditions, i.e., no chopped illumination of sample chamber 22, the temperature distribution about grids 42 and 44 is as shown in FIG. 4(a).

Figure 4:
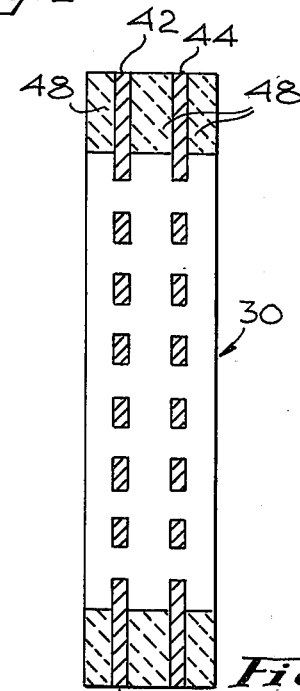

In the case of illumination of sample chamber 22 the gas pressure therein rises causing gas to flow through element 28 from left to right in FIG. 4 (from sample chamber 22 to reference chamber 24 in FIG. 1). The temperature distribution about grids 42 and 44 takes the shape shown in FIG. 4(b) because heated gas from grid 42 flows over grid 44 and is further heated.

Conversely, when gas flows from right to left in FIG. 4 the temperature distribution around grids 42 and 44 takes on the shape shown in FIG. 4(c). For example, if the nickel grids are in an atmosphere of 5% $SO_2$, 10% He and 85% Ar and subject to 49 mA current flow; the temperature of grid 42 can be expected to be about 92° C. while the temperature of grid 44 can be expected to be about 100° C. These nickel grids have identical resistance-temperature characteristics. Using grids 42 and 44 as legs in a Wheatstone bridge, the remaining legs being fixed resistors, an output voltage can be obtained from the bridge, which output corresponds to resistance variations in grids 42 and 44, which variations, in turn, are directly related to gas flow cycling between chambers 22 and 24. Ambient noise has no effect on this flow detector.

Using the photoacoustic spectrometer of FIG. 1 delicate living organisms (along with many other substances) may be non-destructively analyzed.

Figure 5:
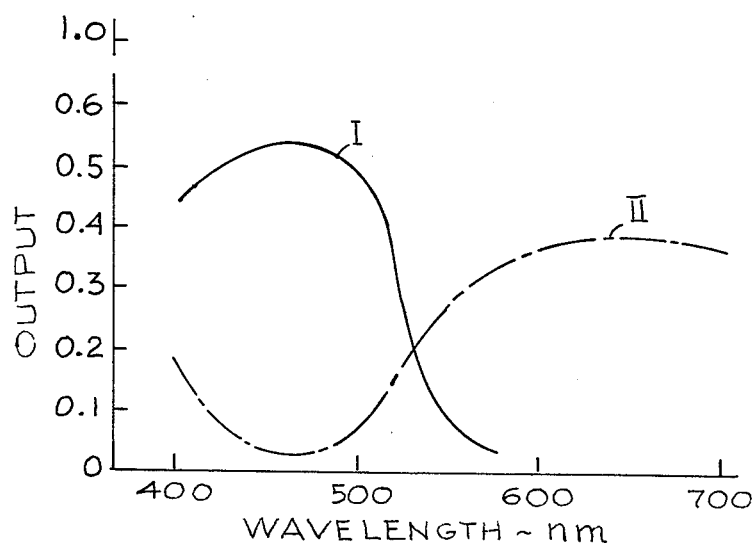
FIG. 5 shows the response curves for several samples analyzed with the apparatus of this invention.

For example, if red ink is placed in sample chamber 22 and analyzed over the range of 400 nm. to 700 nm., curve I in FIG. 5 is produced. On the other hand, if blue ink is placed in the sample chamber and illuminated by chopped, monochromatic light, curve II in FIG. 5 is produced.

Figure 6:
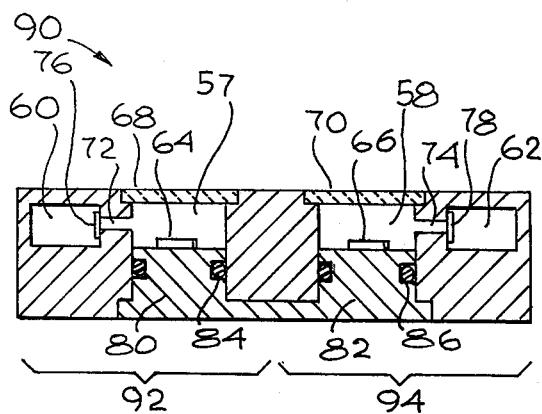
FIG. 6 shows an extension of this invention to multiple, horizontally disposed photoacoustic cells.

The photoacoustic spectrometer according to the present invention may be extended to the multiple-cell configuration of FIG. 6.

In FIG. 6, unit 90 includes cell 92 and cell 94 having sample chambers 57 and 58, respectively, and reference chambers 60 and 62, respectively. Samples 64 and 66 may be illuminated simultaneously or sequentially through respective windows 68 and 70. Chopped light fluxes with identical energy levels are used to illuminate the samples. The gas-flows through the respective orifices 72 and 74 are measured by flowmeter grid assemblies 76 and 78, respectively. Sample beds 80 and 82 are removable but sample chambers 57 and 58 are hermetically sealed (except for orifices 72, 74, respectively), when the beds are in place, by reason of O-rings 84 and 86, respectively.

Figure 7:
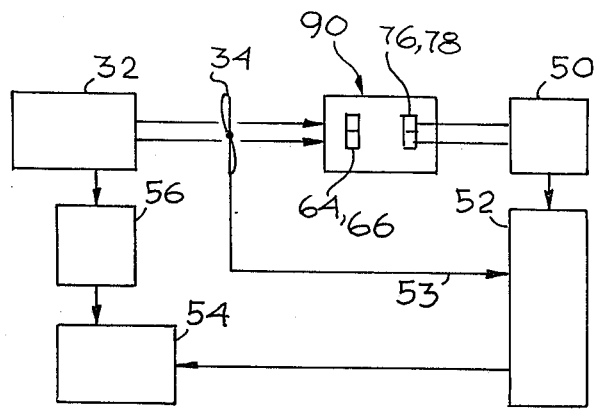
FIG. 7 is a block diagram representing a photoacoustic spectrometer incorporating the cells of FIG. 6.

The system incorporating multi-cell unit 90 is shown in FIG. 7. In that Figure, comparative qualitative analysis of materials in chambers 57 and 58 may be made simultaneously under identical or similar conditions. It is thus possible to detect fine differences between samples 64 and 66 and, further, to calculate, in real time, by means of conventional operational amplifiers in unit 52, the product, sum, quotient or remainder derived from manipulation of corresponding values of the spectra of the two samples 64, 66.

The two cells 92 and 94 comprising unit 90 are gas filled, as described in connection with FIG. 1. The operation of each cell in unit 90 corresponds to the operation of cell 10 in FIG. 1. Similarly the operation of the system of FIG. 7 corresponds to the operation of the system of FIG. 2, except that, in FIG. 7, the analysis of two samples simultaneously is contemplated. Flowmeter grids 76, 78 operate on the same principle as flowmeter grid 28 in FIG. 1 i.e., they are legs in Wheatstone bridges included in bridge-pre-amp circuit 50. In the event that samples 64, 66 are identical in constituency, the outputs of flowmeter grids 76, 78 may be added to give the final signal. Further, those outputs may be multiplied, divided and substracted, as required. Taking one sample as a reference, data from the other may be readily normalized and determination of the relative characteristics of materials can take place accurately and rapidly.

As an example of the use of the multi-cell unit of FIG. 6, with cells 92 and 94 filled with nitrogen gas, Curve I shows a spectrometric comparison of red ink and white paper. Curve II is a spectrographic analysis of blue ink referred to white paper. Curve III shows the results of using this spectrometer to compare red ink to blue ink.

The red ink is placed in a receptacle in chamber 57. White paper is placed in a similar receptacle in chamber 58. Monochromatic light is derived from source 32, which may be a xenon lamp followed by a monochromator utilizing spectral diffraction. The light is split, by conventional techniques such as by use of a prism, into two beams of equal intensity, such beams being chopped by chopper 34 and supplied to chamber 57 and 58 through windows 68 and 70. The wavelength of the light is varied between 400 nm. and 700 nm. The chopping frequency is 10 Hz. The resulting response curve is labeled "I" in FIG. 8.

Next, blue ink is used as the sample 64 and curve II (FIG. 8) is produced.

Figure 8:
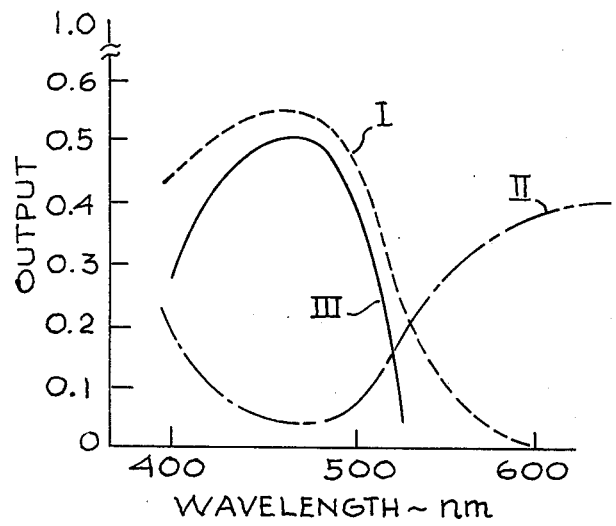
FIG. 8 is a group of response curves derived from the spectrometer of FIG. 7.

Finally, red ink is used as sample 64 and blue ink is used as sample 66. The curve is run, and curve III of FIG. 8 is derived.

Using this technique quantitative differences of the samples can be determined from their qualitative differences.

For analyzing certain biological processes, such as plant responses to sunlight, a monochromatic light source may not be required and, instead, filtered sunlight may be utilized.

Figure 9:
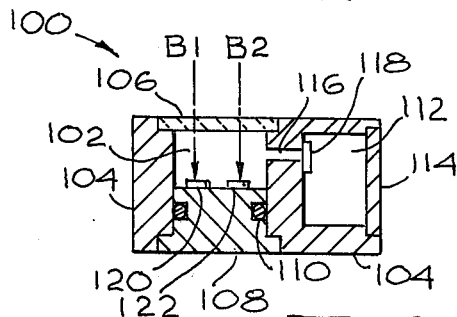
FIG. 9 is an elevational view, partially in section, showing a multiple-sample photoacoustic cell according to the present invention.
Figure 10:
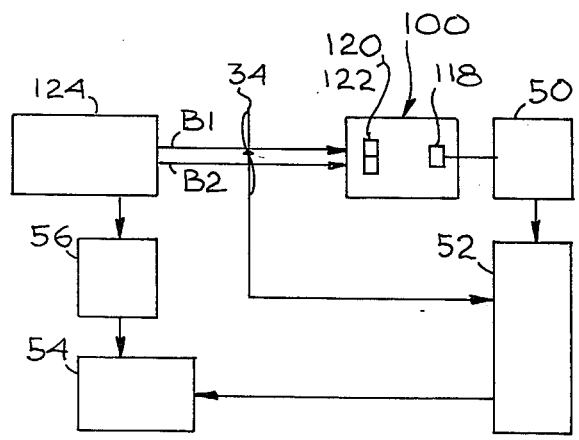

Instead of placing the samples to be compared and analyzed in a pair of cells they may be placed in a single sample chamber and alternately illuminated, as shown in FIG. 9.

In FIG. 9, cell 100 includes sample chamber 102 formed by body 104, transparent window 106 and sample bed 108 sealed in body 104 by O-ring 110. Reference chamber 112 is formed by body 104 and wall 114. Orifice or tunnel 116 permits gaseous communication between sample chamber 102 and reference chamber 112.

Flowmeter element 118 acts as a hot-wire anemometer, as previously described.

Sample bed 108 carries thereon two (or more) samples 120, 122.

Two beams of chopped monochromatic light (where there are two samples) B1 and B2 illuminate samples 120 and 122, alternately with equal periods and intensity of illumination. More samples may be analyzed simultaneously with corresponding numbers of light beams of equal periodicity and intensity.

Figure 10:
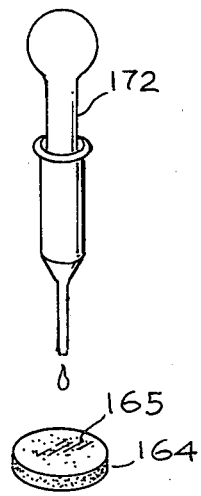
FIG. 10 is a block diagram of a spectrometer using the photoacoustic cell of FIG. 9.

The system is shown schematically in FIG. 10.

Source 124 is similar to source 32 in FIG. 2 except that source 124 is of the dual-flux type providing two beams B1 and B2 of monochromatic light of equal frequency and intensity. The source may utilize a laser or lasers or may use spectral diffraction of light from a Xenon lamp along with beam splitting. The beams are alternately cut-off or chopped by chopper 34 and samples 120 and 122 are alternately illuminated in cell 100. The gas in sample chamber 102 is heated in response to heat flowing from samples 120 and 122 as they are illuminated through window 106 by beams B1 and B2. The heating of the gas in sample chamber 102 causes a pressure rise therein and a flow through orifice 116 to reference 112 past flowmeter element 118. Flowmeter element 118 is in a Wheatstone bridge circuit which is part of the bridge-preamplifier circuit 50 and changes in the resistances of the grids in element 118 cause an a.c. output from bridge.

This a.c. output is amplified and rectified in circuit 52. The d.c. voltage from circuit 52 is fed to computing and indicating section 54 which receives light frequency information from frequency control unit 56 of monochromatic light source 124 and correlates flowmeter signal output with light frequency to produce a display and a chart recording.

Figure 11A:
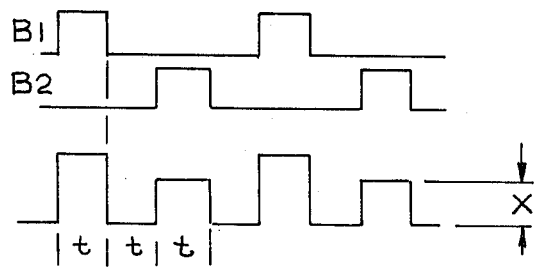
FIGS. 11(a), 11(b) and 11(c) are output-signal graphs for the apparatus of FIG. 9.
Figure 11B:
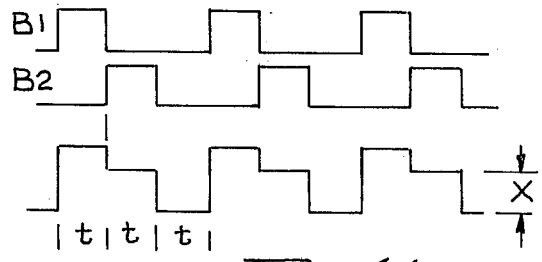
Figure 11C:
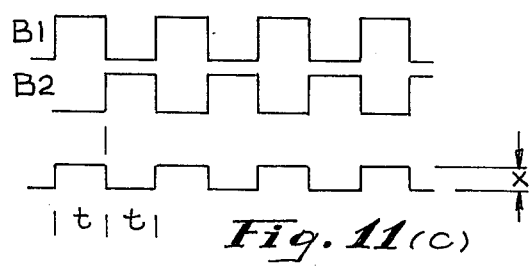

Three modes of illuminating samples 120 and 122 are possible and are illustrated in FIGS. 11(a), 11(b) and 11(c). In FIG. 11(a) the conditions which prevail in cell 100 when samples 120 and 122 are alternately illuminated, are represented. Curve B1 represents the time-varying light flux applied to sample 122. Curve X shows the time variation of pressure in sample chamber 102 when sample 120 is illuminated and Curve Y shows the time variation of pressure in sample chamber 102 when sample 122 is illuminated. The period "t" is representative of the periodicity of chopper 34. Separate output signals result at sensor 118 from the alternate illumination of samples 120 and 122. After amplification by preamplifier 50 the output signals resulting from illumination beams B1 and B2 may be operated upon in operational amplifiers, included in circuit 52 to produce the sum, remainder, product or quotient of those signals. Normalization of the data from either sample can be achieved by comparing it with the data obtained from the other sample.

FIG. 11(b) shows the pressure variation in chamber 102, and hence the output signal from element 118, if the period between illumination pulses is shortened.

FIG. 11(c) shows the results of a still higher frequency chopping and, further, shows the difference signal which can be developed under these illumination conditions. Use of a difference signal improves the signal-to-noise ratio in the output signal from cell 100.

Figure 12:
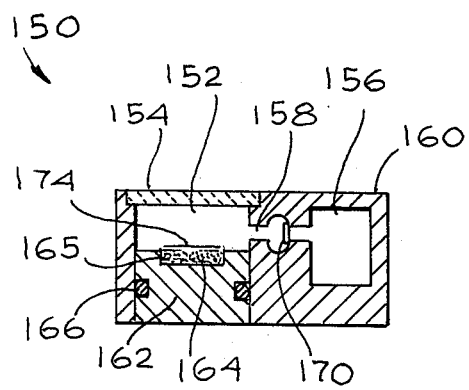
FIG. 12 is a sectional view of an alternate embodiment of a photoacoustic cell according to the present invention.
Figure 13:
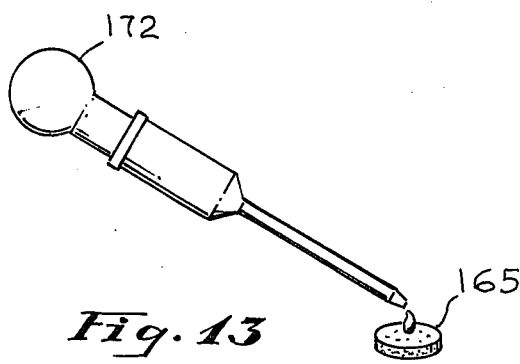
FIG. 13 is a schematic representation of certain apparatus usable in connection with this invention.

In some applications of spectrometry it is desirable to be able to analyze very dilute solutions of one or more compounds. In prior art photoacoustic spectrometry this was a difficult task. FIGS. 12 and 13 show how such anaylses can be achieved with the present invention.

In FIG. 12 cell 150 has sample chamber 152, which may be illuminated through window 154, and reference chamber 156 which is joined to sample chamber 152 by tunnel or orifice 158 in body 160. Sample bed 162 includes a recess 164 filled with a porous material, such as filter paper. Sample bed 162 is removably positioned in body 160 and held therein, in sealed fashion, by O-ring 166. Flowmeter grid or sensor 170 detects gas flow between chambers 152 and 156.

A solution to be analyzed is applied to porous insert 165 by means of a syringe 172, for example, as shown in FIG. 13.

Capillary effect keeps a layer 174 of the solution of the surface of material 165 for ease of analysis.

Figure 14:
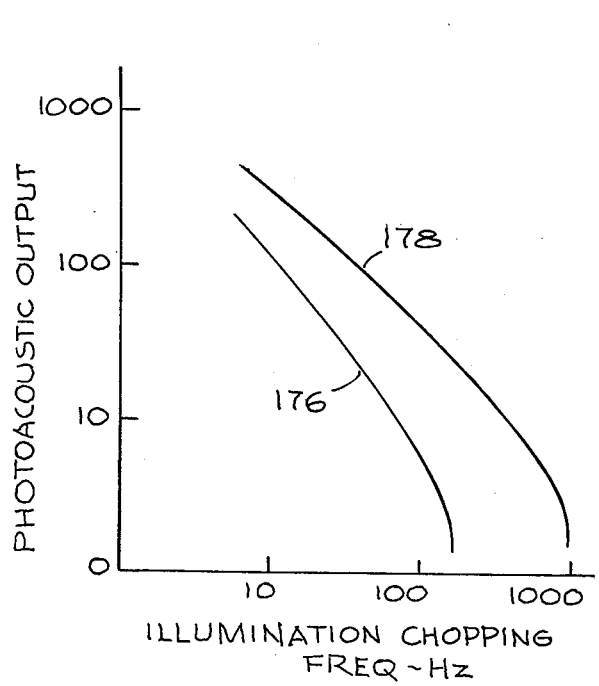
FIG. 14 is a graphical representation of certain photoacoustic output characteristics for differing thicknesses of film being analyzed.

In FIG. 14, curve 176 shows the output signal from sensor 170 versus light chopping frequency for a thin film as sample 174. Curve 178 shows the results when sample 174 forms a thick film on porous substance 164.

Figure 15:
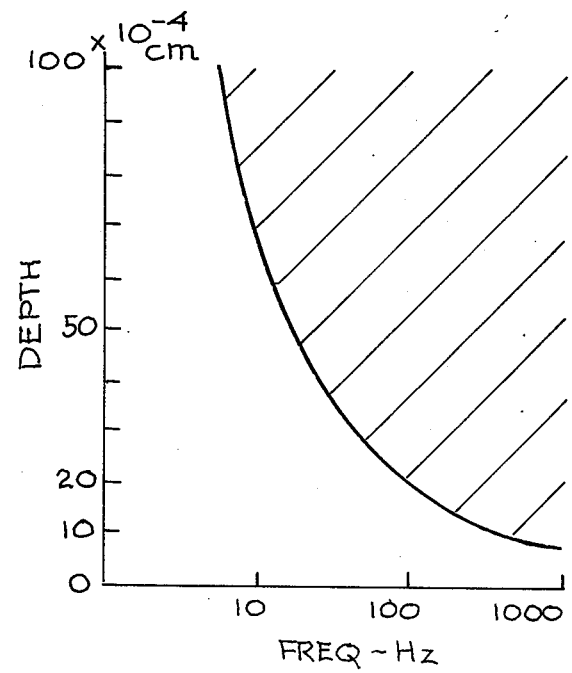
FIG. 15 is a graphical representation of the effective depth of analysis versus frequency of incident monochromatic light for the method according to the present invention.

FIG. 15 shows the relationship between chopping frequency and effective depth of light-to-heat conversion in an illuminated sample.

Figure 16:
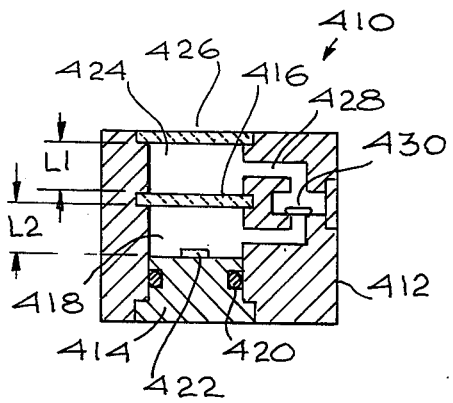
FIG. 16 is a cross sectional view of an additional embodiment of a multi-celled spectrometer according to the present invention.

In FIG. 16, photoacoustic cell 410 includes cell block 412 of opaque, gas-tight material. Block 412, in combination with sample bed 414 and transparent window 416, forms sample chamber 418. Sample bed 414 is hermetically, but removably, sealed in block 412 by O-ring 420. One or more samples 422 rest on bed 414.

Reference chamber 424 is formed between window 416 and transparent window 426, within block 412.

Reference chamber 424 is joined to sample chamber 418 by orifice or tunnel 428. Interposed in tunnel 428 is thermal flowmeter sensor element 430, which is described more fully in connection with FIGS. 3 and 4.

The space within cell 410 is filled with air, helium or nitrogen, for example.

Sample 422 may be in solid, liquid or granular form. A container, not shown, may be desirable to hold sample 22.

Figure 17:
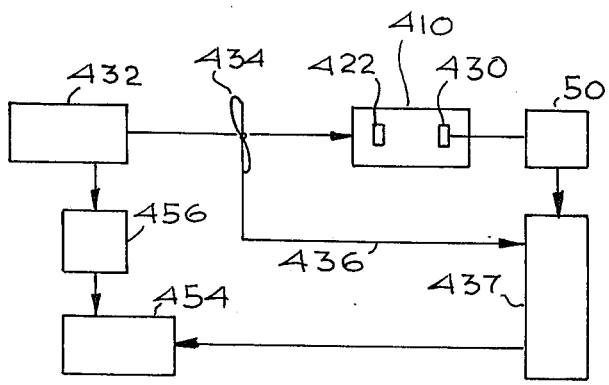
FIG. 17 is a block diagram of a spectrometer using the stacked-cell structure of FIG. 16.

FIG. 17 shows cell 410 in a spectrometer system. In FIG. 17 light source 432 provides a monochromatic light of variable frequency which is chopped by chopper 434 at a speed which may be varied. The rate of chopping may be provided in the form of a synchronizing or reference signal through connector 436 to amplifier-rectifier 437.

Monochromatic light source 432 provides light at a pre-determined wavelength. This light may be obtained by spectral diffraction of light from a xenon lamp or from a laser of known characteristics. The wavelength should be variable over a predetermined range.

Light from source 432 is periodically interrupted by chopper 434 before it is incident upon sample 422. The chopping rate of chopper 434 is variable over a range of frequencies, for example from zero to 1000 Hz.

The light energy incident upon sample 422 through windows 416 and 426 is absorbed, in part, by sample 422 and the absorbed light is converted into heat energy which flows into the surrounding gas in sample chamber 418, causing increased pressure in that chamber and a consequent flow of gas through tunnel 428 and past flowmeter detector element 430 into reference chamber 424 which is of the same path length for light as sample chamber 418, but lacks the heat generating sample 422 and, therefore, exhibits lower pressure than sample chamber 418 during illumination of sample 422.

The interruption of illumination of sample 422 by chopper 434 causes a periodic rise and fall of the temperature of the gas in sample chamber 418 and a consequent oscillatory flow of gas through tunnel 428. The period of that oscillation is identical with the period or frequency of the chopping action by chopper 434. The frequency of the chopping action may be set anywhere between just over 0 Hz to 1000 Hz. The oscillatory flow of gas through tunnel 428 is detected by flowmeter element 430, the characteristics of which are described more fully in connection with FIGS. 3 and 4.

In general, when a substance is irradiated with light the light is partially absorbed by the substance and the absorbed energy is converted into heat. The absorption spectrum is peculiar to each substance and thus the substance may be identified by its absorption characteristics.

In this invention it is important that the light path length L1 through the reference cell and the light path length L2 through the sample cell be equal so that pressure changes due to the existence of the gas, alone, in the two chambers are equal and the only pressure changes which cause gas flow between chambers 418 and 424 are those arising from light absorption in sample 422.

The operation of flowmeter element 430 is identical with that of element 28 in FIG. 2. The associated elements in the diagram of FIG. 17 operate similarly to corresponding elements in FIG. 2.

Figure 18:
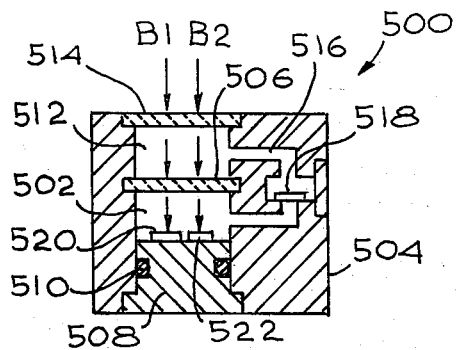
FIG. 18 is a cross-sectional view of a dual-beam version of the embodiment of FIG. 17.
Figure 19:
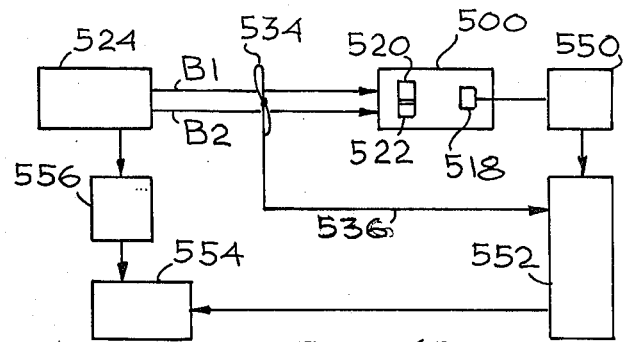
FIG. 19 is a block diagram of a photoacoustic spectrometer utilizing the structure of FIG. 18.

Comparative qualitative analysis of two samples may be made simultaneously by the configuration shown in FIGS. 18 and 19. In FIG. 18, cell 500 includes sample chamber 502 formed by body 502, transparent window 506 and sample bed 508 sealed in body 504 by O-ring 510. Reference chamber 512 is formed by body 504, wall 504 and window 514. Orifice or tunnel 516 permits gaseous communication between sample chamber 502 and reference chamber 512. Flowmeter element 518 acts as a hot-wire anemometer, as previously described.

Sample bed 508 carries thereon two (or more) samples 520, 522.

Two beams of chopped monochromatic light (where there are two samples) B1 and B2 illuminate samples 520 and 522, alternately with equal periods and intensity of illumination. More samples may be analyzed simultaneously with corresponding numbers of light beams of equal periodicity and intensity.

The system is shown schematically in FIG. 19.

Source 524 is similar to source 32 in FIG. 2 except that source 524 is of the dual-flux type providing two beams B1 and B2 of monochromatic light of equal frequency and intensity. The source may utilize a laser or lasers or may use spectral diffraction of light from a Xenon lamp along with beam splitting. The beams are alternately cut-off or chopped by chopper 534 and samples 520 and 522 are alternately illuminated in cell 500. The gas in sample chamber is heated in response to heat flowing from samples 520 and 522 as they are illuminated through windows 506 and 514 by beams B1 and B2. The heating of the gas in sample chamber 502 which can be traced to light absorption by samples 520 and 522 causes a pressure rise therein and a flow through orifice 516 in reference chamber 512 past flowmeter element 518. Flowmeter element 518 is in a Wheatstone bridge circuit which is part of the bridge-preamplifier circuit 550 and changes in the resistances of the grids in element 518 cause an a.c. output from the bridge.

This a.c. output is amplified and rectified in circuit 552. The d.c. voltage from circuit 552 is fed to computing and indicating section 554 which receives light frequency information from frequency control unit 556 of monochromatic light source 524 and correlates flowmeter-sensor signal output with light frequency to produce a display and a chart recording. Chopping rate and phase information may be fed on conductor 536 to detector-amplifier 552 for synchronizing.

Three modes of illuminating samples 520 and 522 are possible as was illustrated in FIGS. 11(a), 11(b), and 11(c). The analysis which applied there applies here. Also see FIGS. 8, 13, 14 and 15 and the discussion thereof.

Figure 20:
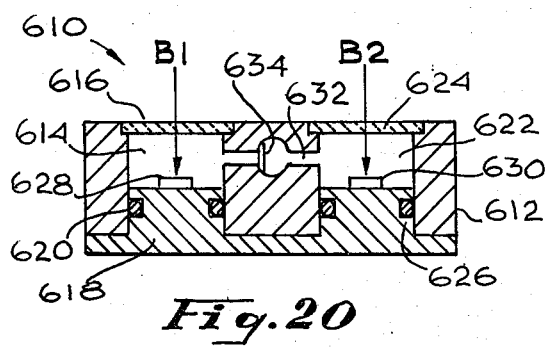
FIG. 20 is a cross-sectional view of an additional multiple-cell configuration.

In FIG. 20, photoacoustic cell 610 includes body 612 of opaque, gas-impermeable material, such as metal. Sample chamber 614 is formed within body 612 by body 612, transparent window 616 and sample bed 618 which is removably carried in body 612 by hermetically-sealing O-ring 20.

Sample chamber 622 is formed by body 612, transparent window 624 and removable sample bed 618 which carries O-ring 626 for chamber sealing purposes.

Sample bed 618 carries thereon two (or more) samples 628 and 630.

A tunnel or orifice 632 joins chambers 614 and 622 for fluid (gaseous) flow therebetween. Thermal flowmeter element 634 is positioned in the path of gaseous flow through tunnel 632 and acts as a hot-wire anemometer. Cell 610 is filled with a gas such as nitrogen, helium or air, and is hermetically sealed with respect to the outside atmosphere.

Two beams of chopped monochromatic light (where there are two samples) B1 and B2 illuminate samples 628 and 630, alternately, or simultaneously, with equal periods and intensity of illumination. More samples may be analyzed simultaneously with corresponding numbers of light beams of equal periodicity and intensity.

Figure 21:
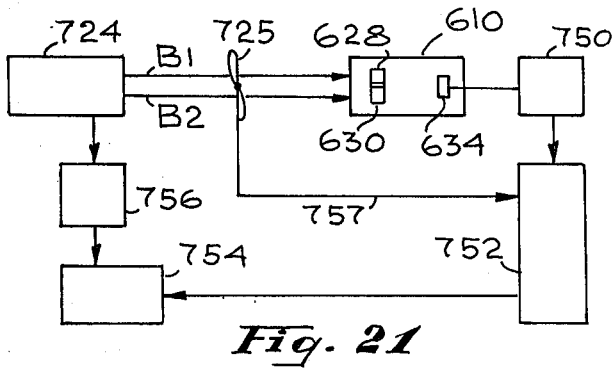
FIG. 21 is a block diagram of a photoacoustic spectrometer using the cell structure of FIG. 20.

The system is shown schematically in FIG. 21.

Source 724 is of the dual-flux type providing two beams B1 and B2 of monochromatic light of equal frequency and intensity. The source may utilize a laser or lasers or may use spectral diffraction of light from a Xenon lamp along with beam splitting. The beams are alternately or simultaneously cut-off or chopped by chopper 725 and samples 628 and 630 are alternately or simultaneously illuminated in cell 610. The gas in each sample chamber is heated in response to heat flowing from samples 628 and 630 as they are illuminated through windows 616 and 624 by beams B1 and B2. The heating of the gas in sample chamber 614 causes a pressure rise therein and a flow through orifice 632 to chamber 622 past flowmeter sensor element 634 (assuming the pressure in chamber 614 exceeds that in chamber 622). Flowmeter element 634 is in a Wheatstone bridge circuit which is part of the bridge-preamplifier circuit 650 and changes in the resistances of the grids in element 634, as a result of gas flow, cause an a.c. output from the bridge. Conversely, if the gas pressure in chamber 622 exceeds that in chamber 614 a reverse gas flow occurs producing an output signal from element 634.

This a.c. output is amplified and rectified in circuit 652. The d.c. voltage from circuit 652 is fed to computing and indicating section 654 which receives light frequency information from frequency control unit 656 of monochromatic light source 624 and correlates flowmeter signal output with light frequency to produce a quantative display and a chart recording. Chopping frequency and phase information is fed by conductor 657 to detector-amplifier 652 from chopper 625. Frequency-to-amplitude coversion can be accomplished by commonly available operational amplifiers which need not be described here.

Figure 22:
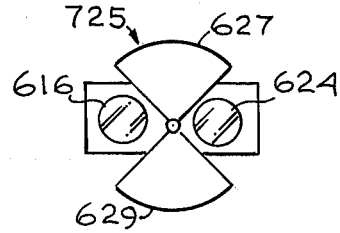
FIG. 22 is a schematic diagram of a chopper for use with the cells of FIG. 20.
Figure 24:
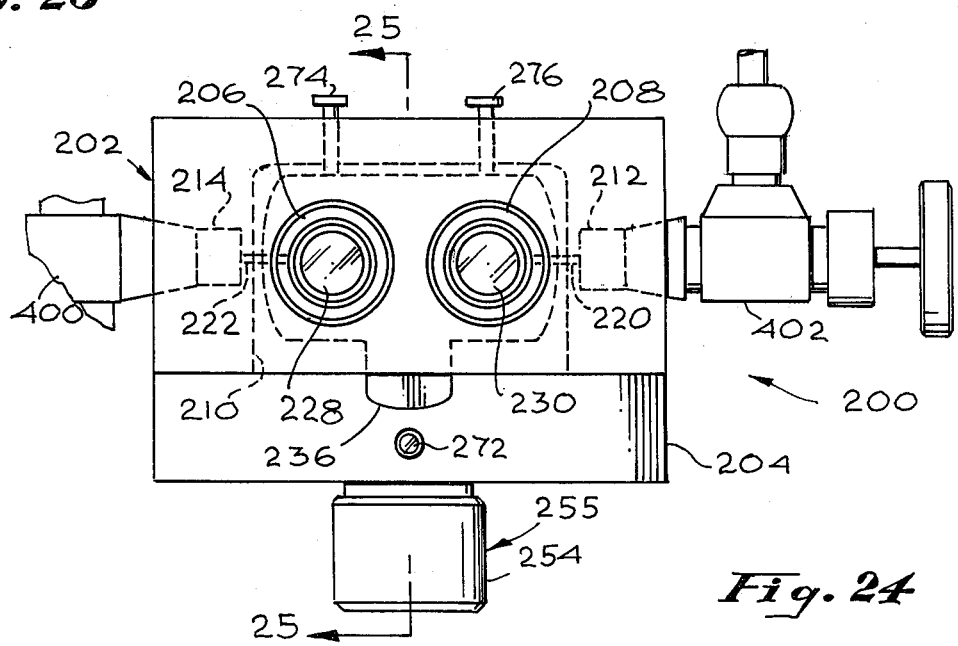
FIG. 24 is a plan view of a multiple-cell spectrometer according to the present invention.

In FIG. 22 chopper 725 is shown with its sectors 627, 629 positioned with respect to windows 616 and 624 so as to permit simultaneous, though intermittent, illumination of samples 628, 630 which lie behind windows 616, 624. The chopping frequency may lie between just over zero Hz and 1000 Hz.

Figure 23:
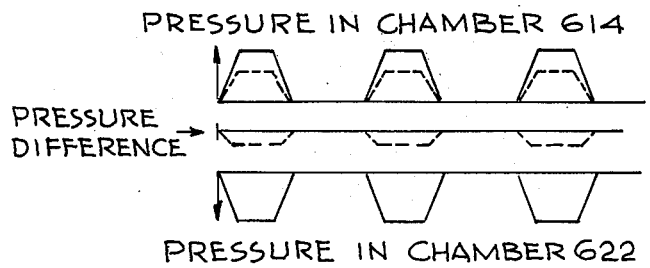
FIG. 23 is a pressure diagram for the cells of FIG. 20.

When samples 628 and 630 are simultaneously illuminated by beams B1 and B2, as they would be with the chopper sectors positioned as shown in FIG. 22, the beams B1 and B2 being of equal intensity and wavelength, the pressure rise in chambers 614 and 622, respectively, as a result of the direct heating of the gas therein by light beams B1 and B2, is equal and there is no output from sensor 634. On the other hand, if sample 630 in chamber 622 exceeds in light absorption capability the corresponding characteristic of sample 614, a greater heat flow will occur from sample 630 into the gas surrounding it in chamber 622 and the gas pressure in chamber 622 will exceed that in chamber 614. The resulting pressure curves are shown in FIG. 23. The pressure differential is shown in curve 23(b). This differential will cause a periodic gas flow past sensor 634 and an output signal having the shape of curve 23(b). By rectifying this signal in unit 752 a voltage representative of the magnitude of the pressure differential between chambers 614 and 622 can be derived and displayed, by a chart recorder or otherwise in calculator-display 754, as a function of wavelength of light in beams B1 and B2, as shown in FIG. 8. Such a display will disclose minute compositional differences between samples 628 and 630, hence the reference to photoacoustic spectrometry. The operation of the flowmeter element 634 and its associated circuits has been described in connection with FIGS. 2, 3 and 4.

FIGS. 24 through 39 give more mechanical details of the photoacoustic spectrometer cell according to this invention.

In FIGS. 24 through 39 unit 200 includes detector block 202 and mounting block 204. Detector block 202 has two vertical openings 206 and 208, the axes of which are parallel. Detector block 202 also has a recess 210, which can be seen more clearly in FIGS. 24 and 26. Reference chambers 212 and 214 are also provided in block 202 and are connected, for gas or other fluid flow, to vertical openings 208 and 206 by tunnels or orifices 220 and 222, respectively. Thermal flowmeter elements or grids 224 and 226 are provided at one end of each of the orifices 222 and 220, respectively. Transparent covers or windows 228 and 230 sealed to detector block 202 at vertical openings 232, 234, permit the introduction of light flux into sealed sample chambers 232 and 234 for illumination of samples supported on sample tray or bed 236.

Mounting block 204 (which may be seen enlarged in FIGS. 28 and 29) has a vertical opening 250 which communicates with recess 210 in detector block 202 when detector block 202 is in position on mounting block 204.

Sample bed support 252 is inserted into opening 250 and is movable in the vertical plane by means of a drive mechanism 255 involving knob 254 and eccentric shaft 256, with intervening or intermediate shaft 258 which receives eccentric shaft 256 in opening 260. (See FIG. 31 for details).

Figure 31:
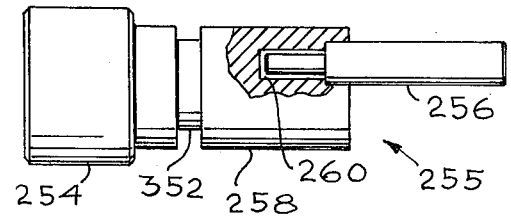
FIG. 31 is a side elevational view, partially sectioned, of a sample-bed-positioning mechanism used in the present invention.

The drive mechanism of FIG. 31 may be easily inserted in mounting block 204 through opening 270.

Screw 272 may be provided to assure fixed vertical positioning of sample bed 236 and also, upon its removal, easy disassembly and removal of sample bed support 252. Horizontal positioning of the sample bed 236 can be acheived by adjusting knobs 274 and 276.

Figure 25:
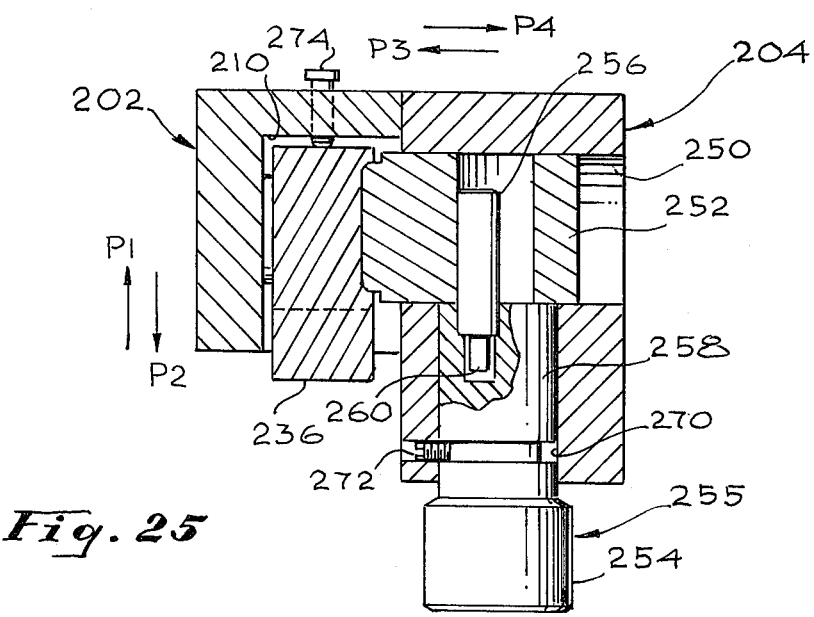
FIG. 25 is a cross-sectional view taken along the line 25—25 in FIG. 24.
Figure 26:
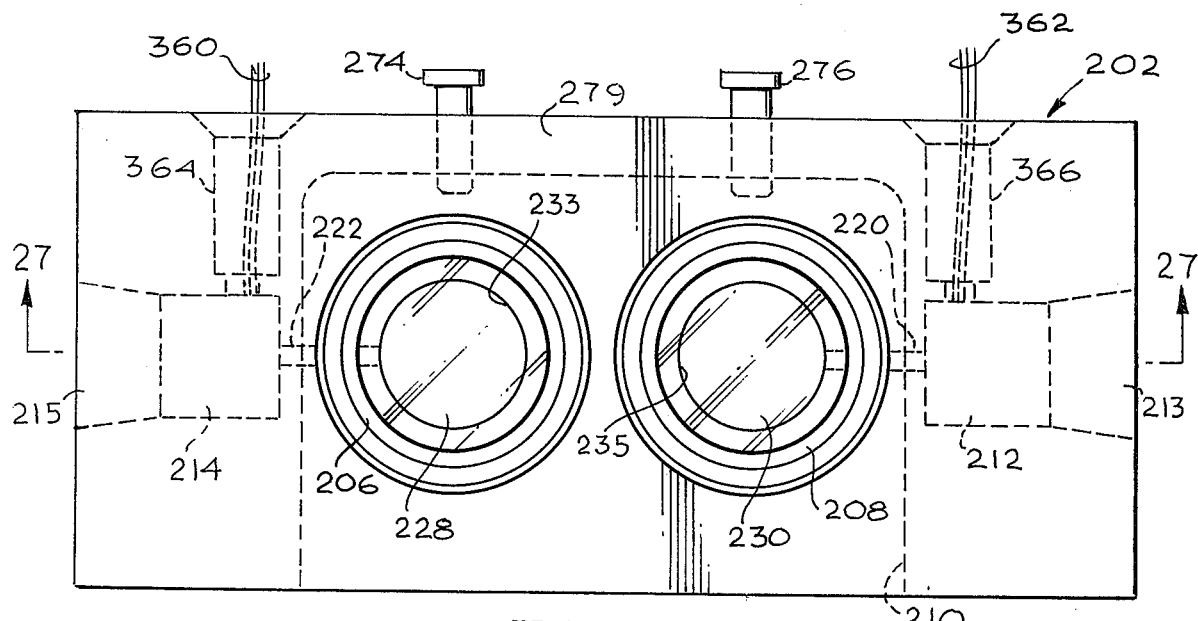
FIG. 26 is a more detailed plan view of the spectrometer of FIG. 24.

The details of detector block 202 are set forth in FIGS. 25 and 26.

Detector block 202 is designed for simplicity of manufacture and assembly. It is box-like in configuration and comprises back portion 273, side portions 275 and 277 and upper portion 279 forming opening or recess 210 for receiving sample tray or bed 236. Screws 274 and 276 are provided for horizontal registration of sample tray 236. Reference chambers 212 and 214 are provided in side walls 277 and 275, respectively. These reference chambers 277 and 275 are in gaseous communication with sample chamber recesses 234 and 232, respectively, through respective tunnels or orifices 220 and 222. At the reference chamber ends of tunnels 220 and 222 are thermal flowmeter sensor elements 226 and 224, respectively. These sensor elements are coupled electrically through cables 362 and 360 to external electrical circuits, not shown through hermetically sealed passages 366 and 364, respectively. Reference chambers 212 and 214 are coupled to tapered openings 213 and 215, respectively. These latter openings are provided for coupling to gas controlling needle valves 402 and 400, respectively, shown in FIG. 24. These valves permit filling of the cells in unit 200 with a gas, such as helium.

Upper wall 279 has two adjacent openings 233 and 235, the axes of which are parallel. Openings 233 and 235 have stepped diameters with the largest diameters occurring at the upper surface of block 202. As a result, shoulders 237 and 239 are formed. Transparent windows 228 and 230 rest on shoulders 237 and 239, respectively. O-rings 241 and 243, engaged by securing rings 206 and 208, assure a gas-tight seal around windows 228 and 230.

Figure 28:
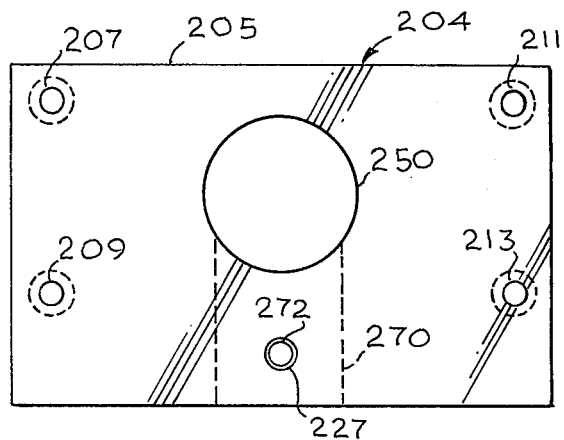
FIG. 28 is a plan view of the base for supporting certain operating portions of the invention.
Figure 29:
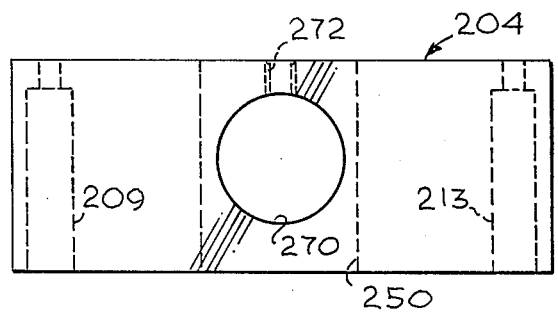
FIG. 29 is an elevational view of the base of FIG. 28.

Mounting block 204 is constructed as shown in FIGS. 28 and 29. It comprises a rectangular block 205 at the center of which is a vertical opening 250. A horizontal opening 270, seen clearly in the side view of FIG. 29, communicates with vertical opening 250.

Figure 33:
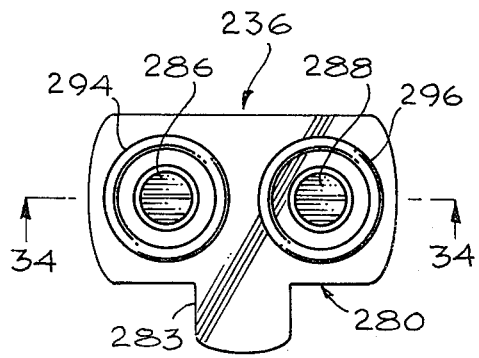
FIG. 33 is a plan view of a sample bed usable in the present invention.
Figure 35:
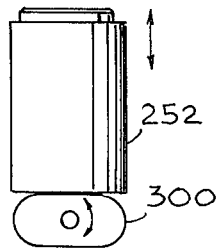
FIGS. 35 through 38 show several examples of sample bed positioning mechanisms for use in the present invention; and, FIG. 39 is a side view of the sample bed portion of FIG. 30.
Figure 36:
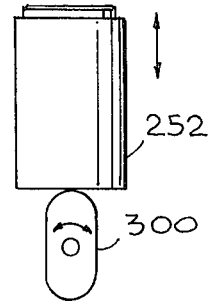
Figure 34:
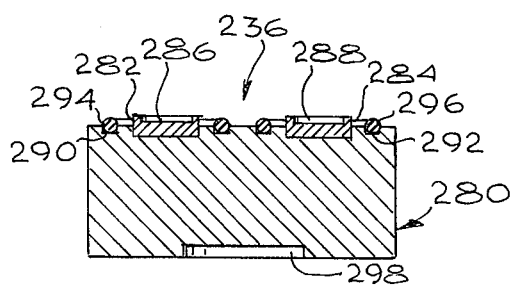
FIG. 34 is a cross-sectional view taken along the line 34—34 in FIG. 33.

Mounting block 204 is held together by screws 207, 209, 211 and 213. Securing screw 272 secures the sample-tray-support drive mechanism through hole 227. The details of bed or tray 236 can be seen most clearly in FIGS. 33 and 34. In FIGS. 33 and 34, sample bed 236 includes main block 280 with tab 282. Block 280 has upper recesses 282 and 284 for receiving sample receptacles or dishes 286 and 288, respectively. Samples 64 and 66 of FIG. 6 may be placed therein.

Figure 27:
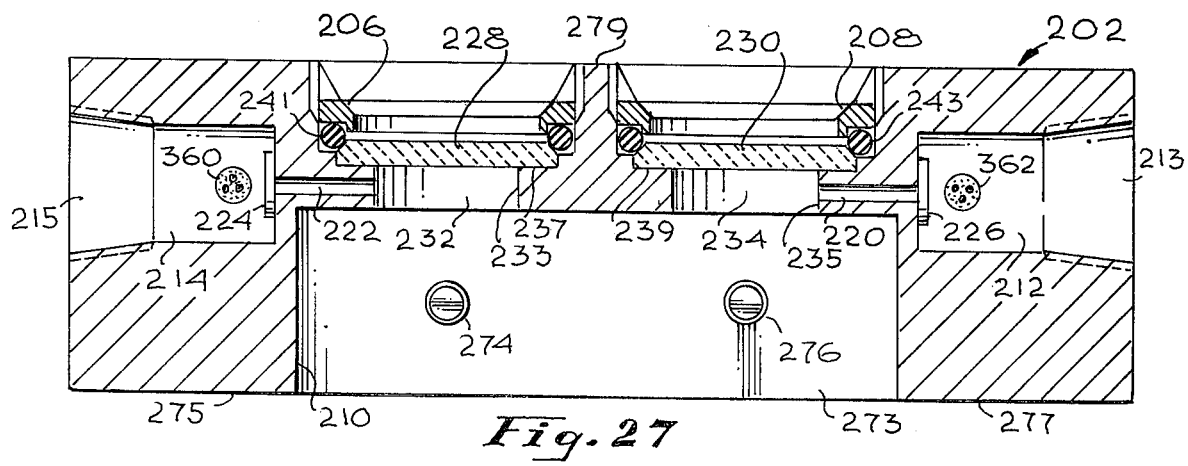
FIG. 27 is a cross-sectional view taken along the line 27-27 in FIG. 26.

Two O-ring slots 290 and 292 are provided in the upper surface of block 280. O-rings 294 and 296 are provided therein. This sample bed 236 has recess 298 in the under side thereof for receiving sample bed support 252, whereby such support may move vertically in space 250 and bed 236 may move vertically in space 210 in response to rotation of knob 254. Because of the eccentricity of shaft 256 in drive shaft or rotator 258, sample table 236 will move up and then down as knob 254 is rotated through 360°. This permits easy positioning and removal of sample bed 236, for removal or replacement of the sample of samples thereon. Moving the sample-bed support upwards causes O-rings 294 and 296 to engage the inner surface of the recess in the detector block 202 thereby forming sealed sample chambers 232 and 234 (FIG. 27). Additional methods for providing vertical motion to sample-bed support 252 and sample bed 236 are shown in FIGS. 35 through 38. FIGS. 28 and 29 show the use of a cam 300 to raise or lower support 252. Cam 300 is activated by knob 254.

Figure 37:
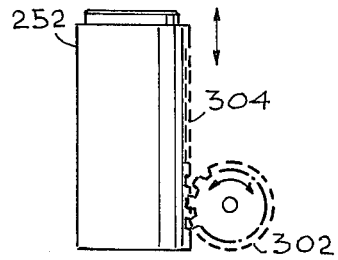

In FIG. 37, a rack and pinion drive is shown. Pinion 302, which is driven from knob 254, drives rack 304 on support 252.

Figure 38:
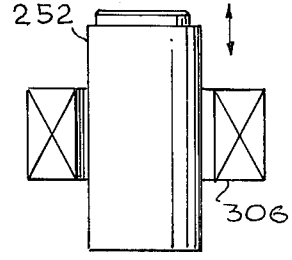

FIG. 38 shows, symbolically, a solenoid plunger drive 306 for support 252.

Figures 30, 39:
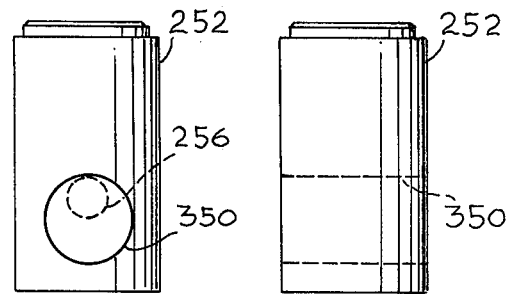
FIG. 30 is a front, elevational view of the sample bed portion of FIG. 29.

FIGS. 30 and 39 show how eccentric shaft 256 cooperates with opening 350 in sample bed support 252 to raise and lower support 252.

Figure 32:
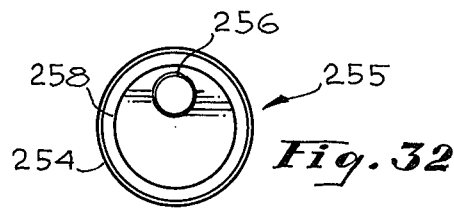
FIG. 32 is an end elevational view of the positioning mechanism of FIG. 31.

In FIGS. 31 and 32, drive mechanism 255 includes knob 254, slot 352 and eccentric shaft 256. Eccentric shaft 256 is positioned in off-axis opening 260 in intermediate shaft or rotator 258.

Removal of screw 272 from slot 352 permits easy removal of drive mechanism 255 and support 252 to facilitate sample changes.

While particular embodiments of the present invention have been shown and described it will be apparent to those skilled in the art that variations or modifications may be made therein without departing from the spirit and scope of the present invention. It is the purpose of the appended claims to cover all such variations and modifications.

What is claimed is:

1. A photoacoustic spectrometer including a mounting block and a detector block carried thereby, said mounting block having a vertically-oriented opening therethrough and a horizontal opening therein communicating with said vertical opening;

support means movably carried in said vertically oriented opening;

vertical adjustment means carried by said horizontal opening and engaging said support means for effecting vertical motion thereof;

said detector block being supported from said mounting block and have an overhanging portion, said overhanging portion including at least one opening therethrough;

said detector block including, in addition, a sample bed portion, said sample bed portion including a recess in the lower surface thereof adapted to receive said support and at least one upper recess in the upper surface thereof adapted to receive a sample dish, said upper recess being positioned to be, in use, aligned with said at least one opening in said overhanging portion of said detector block;

a window covering said upper recess;

an O-ring surrounding said window;

said sample bed portion including, in addition, a reference chamber;

a tunnel fluid-coupling said reference chamber to said upper recess;

a pair of thermo-sensitive elements supported at the reference chamber end of said tunnel and each having terminals for connection to external electrical circuits;

said reference chamber having means for connecting to an external source of a fluid;

said sample bed portion and said "O"-ring being forced into sealing engagement with said overhanging portion upon upward movement of said support means by adjustment of said vertical adjustment means, to form a sealed chamber.

* * * * *